(12) United States Patent
Spector

(10) Patent No.: US 8,642,071 B2
(45) Date of Patent: *Feb. 4, 2014

(54) COMPRESSED ARTICLES WITH MICROENCAPSULATION

(76) Inventor: Donald Spector, New York, NY (US)

( * ) Notice: Subject to any disclaimer, the term of this patent is extended or adjusted under 35 U.S.C. 154(b) by 778 days.

This patent is subject to a terminal disclaimer.

(21) Appl. No.: 11/439,831

(22) Filed: May 23, 2006

(65) Prior Publication Data

US 2007/0275039 A1    Nov. 29, 2007

(51) Int. Cl.
*A61F 13/00* (2006.01)
*B32B 27/04* (2006.01)

(52) U.S. Cl.
USPC .......................................... 424/443; 442/123

(58) Field of Classification Search
None
See application file for complete search history.

(56) References Cited

U.S. PATENT DOCUMENTS

| | | | | |
|---|---|---|---|---|
| 2,952,462 | A * | 9/1960 | Planin | 273/157 R |
| 4,241,007 | A * | 12/1980 | Tanaka et al. | 264/324 |
| 4,780,361 | A | 10/1988 | Schlein | |
| 4,881,915 | A | 11/1989 | Liaw | |
| 5,316,689 | A | 5/1994 | Farrell | |
| 6,034,051 | A | 3/2000 | Lindauer et al. | |
| 6,159,487 | A * | 12/2000 | Znaiden et al. | 424/402 |
| 6,432,272 | B1 | 8/2002 | Hollenberg et al. | |
| 6,900,249 | B2 | 5/2005 | Mork et al. | |
| 2004/0185730 | A1 * | 9/2004 | Lambino et al. | 442/123 |
| 2005/0153862 | A1 * | 7/2005 | Lau et al. | 510/445 |

OTHER PUBLICATIONS

Office Action, U.S. Appl. No. 11/424,152, Mailing Date Jul. 21, 2009.
Geoffrey L. R. Williamson, Response to Office Action, U.S. Appl. No. 11/424,152, Mailing Date Oct. 21, 2009.
David J. Zwick, Response to Office Action, U.S. Appl. No. 11/424,152, Mailing Date Mar. 23, 2009.

* cited by examiner

*Primary Examiner* — Kyle Purdy
(74) *Attorney, Agent, or Firm* — Collard & Roe

(57) ABSTRACT

Microencapsulated materials are added to compressed products. Microencapsulation permits a wide range of products to be incorporated into these compressed products while maintaining the dry, compressed nature of the products. In one aspect, methods are provided that comprise forming the article, that comprises paper or fabric, in a size of intended use; attaching a plurality of microencapsulated beads containing a material therein to the paper or fabric; and compressing the article to a compressed size that is smaller than the size of intended use. In another aspect, articles comprise a liquid-expandable paper or fabric, and a plurality of microencapsulated beads containing a material therein attached to the paper or fabric.

11 Claims, 3 Drawing Sheets

COMPRESSED ARTICLES WITH MICROENCAPSULATION

FIELD OF THE INVENTION

This application relates to the field of compressed paper and woven goods.

BACKGROUND OF THE INVENTION

Products made in a compressed state are small, for example, the size of a coin or a button. When such products are put into a liquid, for example, water, they expand, become larger, and are then suitable for their intended purpose. For example, buttons of compressed paper can be hydrated to be used as wipes. In other examples, compressed fabrics are hydrated to make towels, face cloths, tee shirts, and other clothing. Compressed sponges that expand upon contact with water are another example.

Compressed goods are useful because their light weight and small size make shipping and handling them easier than otherwise. There is a need to provide compressed goods with enhanced features, for example, ones that provide medicinal or comfort therapies.

SUMMARY OF THE INVENTION

Figure 1:
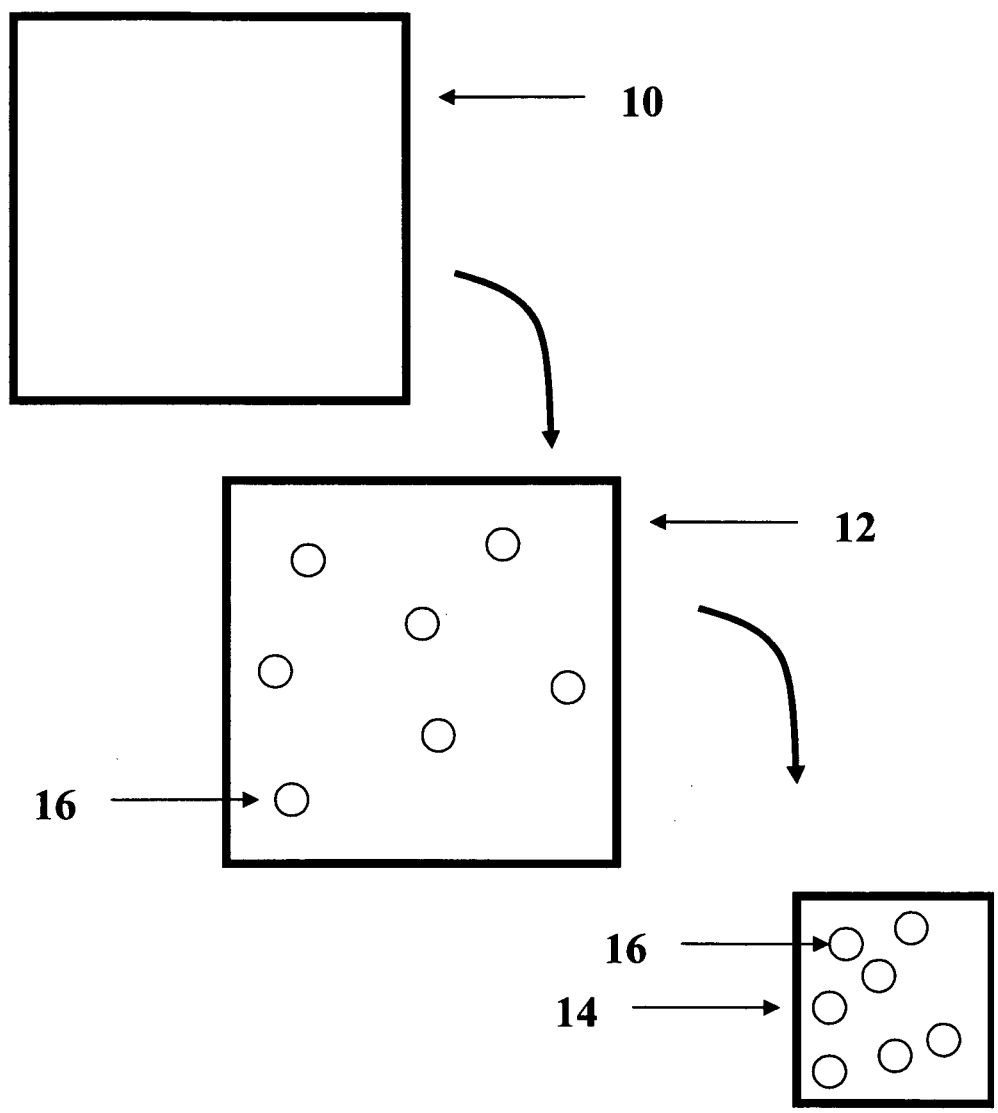
FIGS. 1 and 2 illustrate a compressed cloth having microencapsulated beads in accordance with various aspects of the present invention.

In one aspect of the invention, microencapsulated materials are added to compressed products. Generally, the materials are added to the products before the products are compressed. The microencapsulated products can also be added to the products after they have been compressed.

Microencapsulation permits a wide range of products to be incorporated into these dehydrated compressed products while maintaining the dry, compressed nature of the products. The coatings of microencapsulated beads of material can be soluble in various types of liquid, for example, water. Moreover, in some examples, it may be desirable that the coatings only release material upon mechanical force, e.g., friction.

Methods of making an article are provided, the methods comprising forming the article, that comprises paper or fabric, in a size of intended use; attaching a plurality of microencapsulated beads containing a material therein to the paper or fabric; and compressing the article to a compressed size that is smaller than the size of intended use. In one embodiment, the step of compressing the article comprises dehydrating the article. In another embodiment, the step of compressing the article comprises exposing the article to vacuum pressure. In yet another embodiment, the method further comprises contacting the article with a liquid to expand the article to approximately the size of intended use.

In another aspect of the invention, the articles comprise a liquid-expandable paper or fabric, and a plurality of microencapsulated beads containing a material therein attached to the paper or fabric. Generally, the paper or fabric material is in a compressed state and the material remains compressed until a liquid contacts the material. This application may refer to the compressed paper or cloth as a compressed coin. In some examples, the microencapsulated beads are attached to the surface of the paper or fabric. In other examples, the beads are embedded within the fabric or paper.

In one embodiment, the material is released from the beads upon expansion of the paper or fabric in the liquid. In some examples, the material comprises therapeutic compounds such as antibiotics or alcohols, to be used, for example, for cleaning wounds or other medicinal purposes. Articles having such materials can be useful in military or third world environments. In other examples, the material comprises comforting compounds such as a fragrance, an oil, a skin-moisturizer, or combinations thereof. Articles having such materials can be used as compresses for aromatherapy or other relaxation therapies.

In some embodiments, articles in accordance with the present invention comprise a towel, a face cloth, or a wiping cloth.

There are many uses for the micro encapsulated products in accordance with various aspects of the present invention. One use is combining the compressed coins with coated alcohol or antibiotic. When they are expanded, they then have the ability to be able to be used to clean wounds and other medical uses. This might be of particular value in third world areas or military situations.

Another use is to microencapsulate fragrances and/or oils with these compressed coins. In this application, these coins would be placed in warm water. As they are expanded they can be used as compresses for aromatherapy or other relaxation therapies.

It is believed that there are substantial uses and a substantial business for combining these two technologies. Without the dryness of the microencapsulation it would cause the coins to expand and/or the ingredients to be dissipated.

DESCRIPTION OF A PREFERRED EMBODIMENT

FIG. 1 illustrates one aspect of the present invention. Article 10 is paper, a woven good or cloth. The article 10 can, for example, be made of rayon, but any compressible material can be used.

Microencapsulated beads or materials 16 are added to the article 10 by known techniques to form a new article 12. The microencapsulated beads 16 can be formed to be soluble in a liquid, such as water. In this case, the microencapsulated beads 16 will dissolve upon contact with the liquid and, upon being dissolved, will release the encapsulated material in the beads 16. The microencapsulated beads 16 can also be formed to break upon a pressure or friction being asserted on the beads 16. In this case, the beads 16 will break and release their contents upon the exertion of the pressure.

The article 12 having the microencapsulated beads can be compressed to a smaller size, such as the size of article 14, using any known technique, the techniques including but not limited to dehydration or submitting the article 14 to vacuum pressure. The size of the article 12 is usually small, such as the size of a coin or a button. Other sizes, however, can be used.

The materials in the microencapsulated beads 16 can include an antibiotic, a pharmaceutical, an alcohol, a fragrance, an oil, a skin conditioner, a skin moisturizer, or combinations thereof. Other materials can include cleansers, polishes, anti itch materials and anti-inflammatory materials.

Any number of fragrances can be used. For example, fragrances thought to help calm people can be used. A bubble gum fragrance can also be used to provide a unique bubble bath for children.

Figure 2:
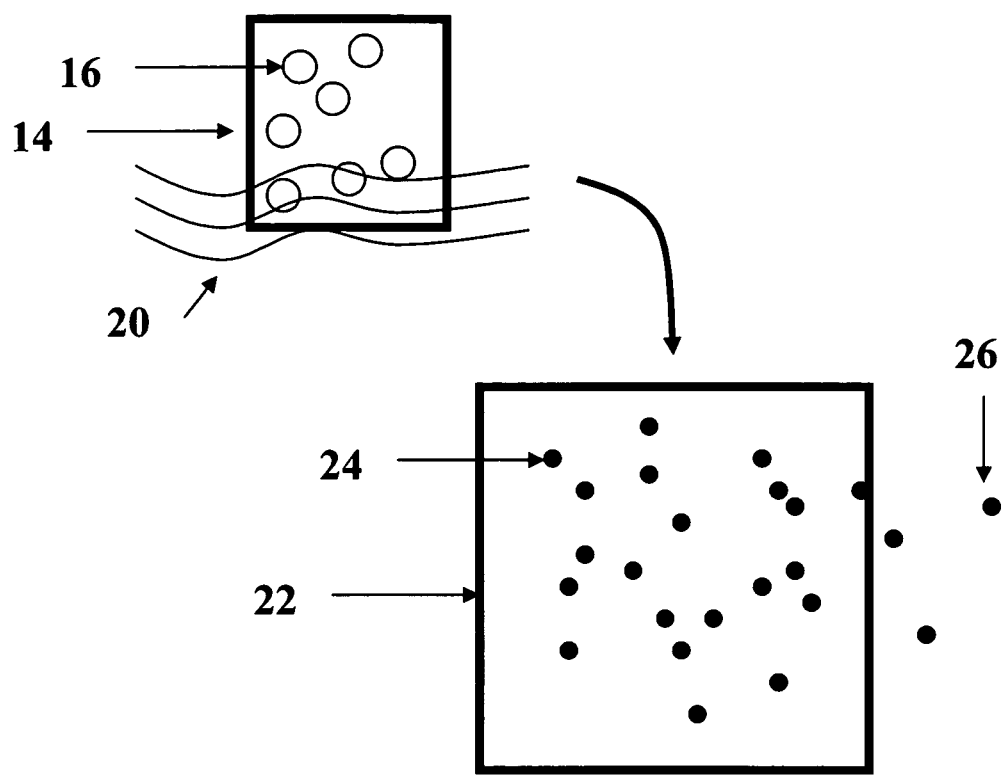

FIG. 2 illustrates the article 14 being exposed to a liquid 20. The liquid 20 can be any liquid that will de-compress the article 14. By way of example, the liquid could be water. The liquid 20, in this case, also preferably dissolves the microencapsulated beads 16 to release the contents of the beads.

The result of the application of liquid 20 is that the article 14 expands to the size of the article 22. The microencapsulated beads 16 have dissolved, releasing the contents 24 and 26. Generally, if the contents of the beads 16 were in liquid form, the contents 24 will stay on the article 22. If the contents of the beads 16 included fragrances, the contents 26 may leave the article 22.

In the case where the microencapsulated beads 16 are broken by friction, the application of the liquid 20 would not dissolve the beads 16. Instead, when the article 22 is rubbed on another article, such as a person's skin, the beads 16 are broken and the contents 24 and 26 are released.

The article 10 can be any compressible material that can be expanded.

Figure 3:
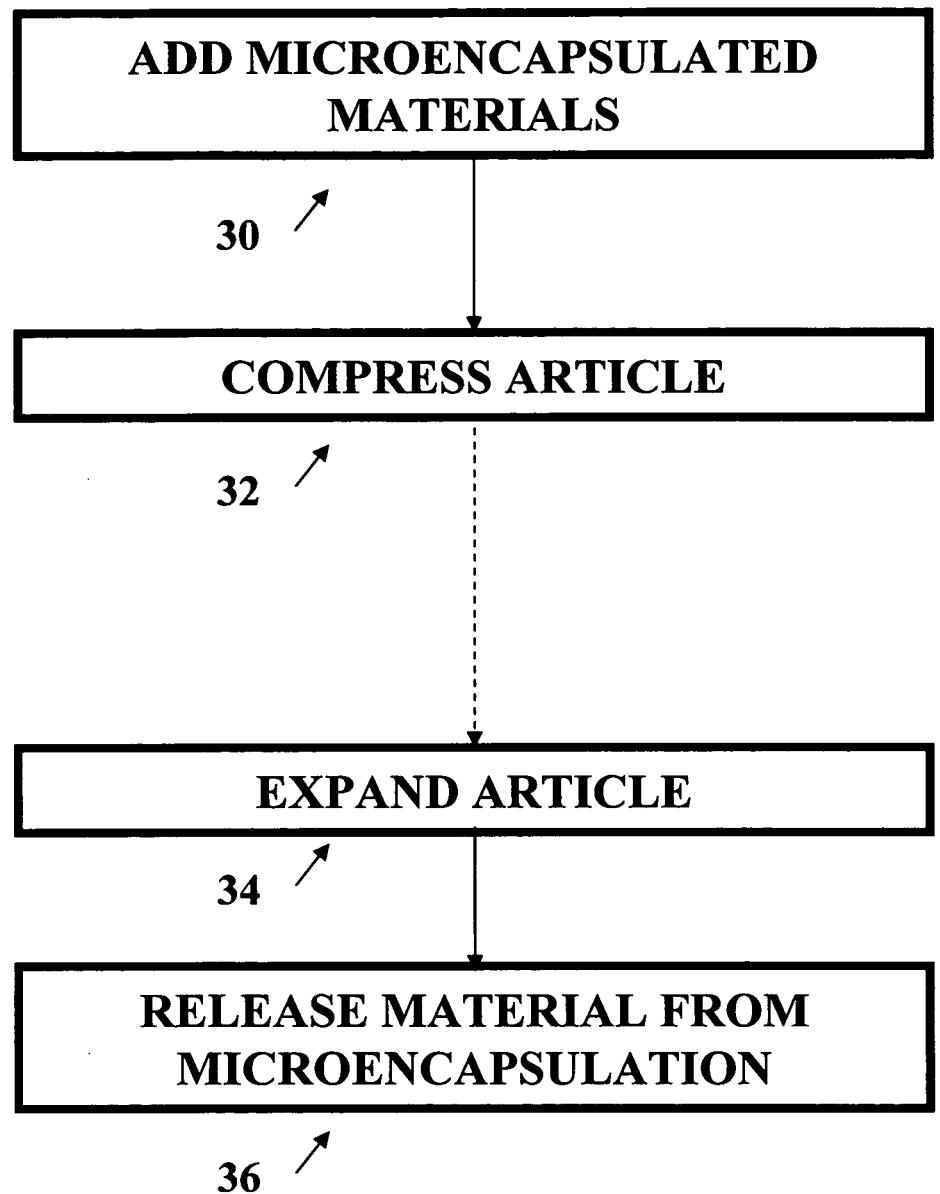
FIG. 3 illustrates a method in accordance with one aspect of the present invention.

FIG. 3 illustrates a method in accordance with one aspect of the present invention. In step 30, microencapsulated beads are added to an article. As stated before, the article can be cloth, a woven material, paper or any compressible material. In step 32, the article is compressed. The order of these two steps can be reversed.

In step 34, the article is expanded. In step 36, the contents of the microencapsulated beads 16 are released either as a result of contact with a liquid or as a result of friction or pressure.

The articles of the present invention can be used, by way of example only, to treat wounds, to provide therapy, such as aroma therapy or relaxation therapy, for bubble baths, for cleaning—both personal and for objects.

In accordance with another aspect of the present invention, the article 10 that is compressed can also be shaped. The article 10 can also have printed material on it. The shape of the article 10 and the printed material preferably have a relation to the article 10 and the material released by the microencapsulated beads 16. For example, if the article 10 is a wash cloth and the microencapsulated material is a bubble gum fragrance so that a child might enjoy a bath, the article 10 can be shaped like a cartoon character and a picture of the carton character can be printed on the article 10. For example, the article 10 could be shaped like Mickey Mouse and a picture of Mickey Mouse could be placed on the article 10.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed:

1. A compressed article of hygiene consisting of:
   a compressed cloth that has been compressed by dehydration or vacuum pressure into a coin shape and that is expandable upon contact with a liquid; and
   a plurality of microencapsulated beads containing a material selected from the group consisting of an antibiotic, an alcohol, a fragrance, an oil, a skin conditioner, a skin moisturizer or combinations thereof, the plurality of microencapsulated beads being embedded within the compressed cloth,
   so that, upon contact with water, expansion of the compressed cloth is unconstrained, and wherein the compressed cloth when expanded has a shape of an object or a character and has printing on the compressed cloth.

2. The article of claim 1, wherein the material is released from the beads upon expansion of the cloth in the liquid.

3. The article of claim 1, wherein the liquid comprises water.

4. The article of claim 1, wherein the material comprises an antibiotic.

5. The article of claim 1, wherein the material comprises an alcohol.

6. The article of claim 1, wherein the material comprises a fragrance.

7. The article of claim 1, wherein the material comprises an oil.

8. The article of claim 1, wherein the material comprises a skin conditioner.

9. The article of claim 1, wherein the material comprises a skin moisturizer.

10. The article of claim 1, wherein the cloth comprises a towel, a face cloth, or a wiping cloth.

11. The article of claim 1, wherein the cloth is rayon.

* * * * *